United States Patent [19]

Westerman

[11] Patent Number: 4,735,200
[45] Date of Patent: Apr. 5, 1988

[54] ORAL HYGIENE APPARATUS

[76] Inventor: Robert D. Westerman, 7931 Jefferson Hwy., Baton Rouge, La. 70809

[21] Appl. No.: 779,128

[22] Filed: Sep. 23, 1985

[51] Int. Cl.[4] .................. A61H 9/00; A61H 13/00; A47K 7/04
[52] U.S. Cl. ........................................ 128/66; 128/53; 128/55; 15/22 A
[58] Field of Search ............... 128/66, 50, 53–55, 128/62 A, 65, 37; 15/22 A, 24, 29; 60/486; 92/47, 48

[56] References Cited

U.S. PATENT DOCUMENTS

| 1,996,467 | 4/1935 | Ernst | 60/486 |
| 2,712,286 | 7/1955 | Kiefer | 92/48 |
| 3,046,585 | 7/1962 | Ledingham et al. | 15/24 |
| 3,476,105 | 11/1969 | Abramowitz | 128/65 |
| 3,551,931 | 1/1971 | Monroe et al. | 128/62 A X |
| 3,631,556 | 1/1972 | Holster et al. | 128/50 X |
| 3,636,947 | 1/1972 | Balamuth | 128/66 |
| 3,645,255 | 2/1972 | Robinson | 128/66 X |
| 3,692,437 | 9/1972 | Ray | 92/48 |
| 3,909,867 | 10/1975 | Hogsell | 15/24 |
| 3,966,359 | 6/1976 | Woog | 128/66 |
| 4,192,035 | 3/1980 | Kuris | 128/62 A X |
| 4,346,492 | 8/1982 | Solow | 128/62 A |
| 4,471,503 | 9/1984 | Smyth | 128/66 |
| 4,534,340 | 8/1985 | Kerr et al. | 15/22 R X |

Primary Examiner—Albert W. Davis, Jr.
Assistant Examiner—Richard R. Cole
Attorney, Agent, or Firm—Helfgott & Karas

[57] ABSTRACT

An apparatus for oral hygiene having a dental handpiece supporting a replaceable dental bit. The dental bit is operated by a fluid actuated driving mechanism in the handpiece causing reciprocation of the dental bit to cause a mechanical cleaning action on contact with dental surfaces. The dental bit has fluid outlet ports associated with it. A source of pressurized fluid is provided for supplying fluid to the interior of the handpiece which serves both to actuate the driving mechanism as well as for providing a supply of fluid to the dental bit for discharge through the outlet ports. The fluid thereby simultaneously imparts a fluid cleaning action to the dental surfaces in addition to the mechanical cleaning action.

27 Claims, 7 Drawing Sheets

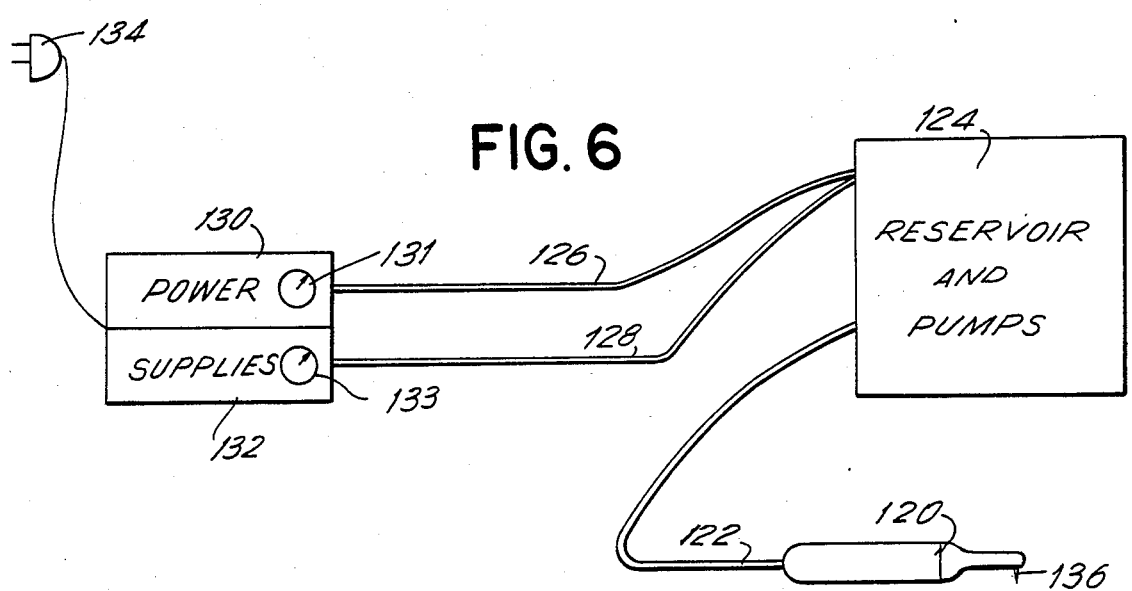

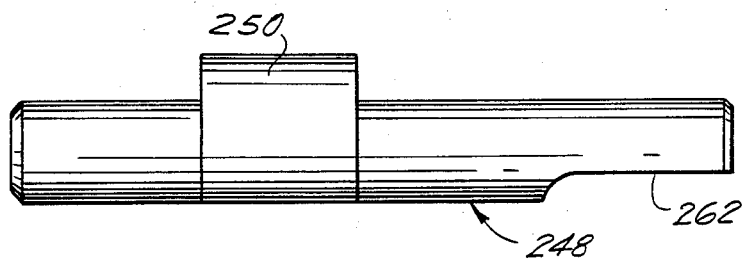
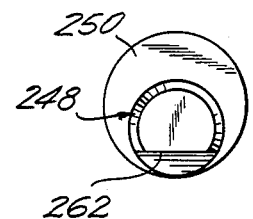
FIG.10A  FIG.10B
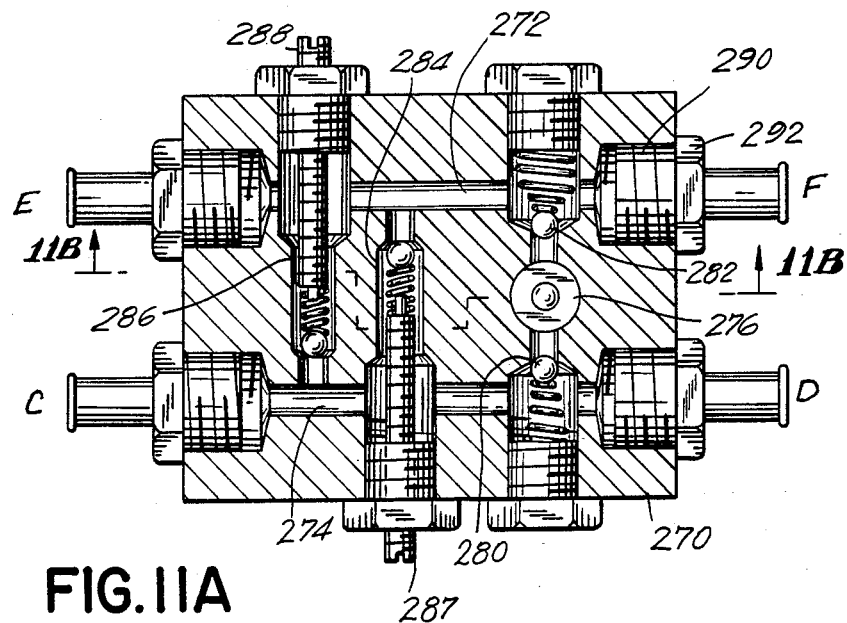
FIG.11A
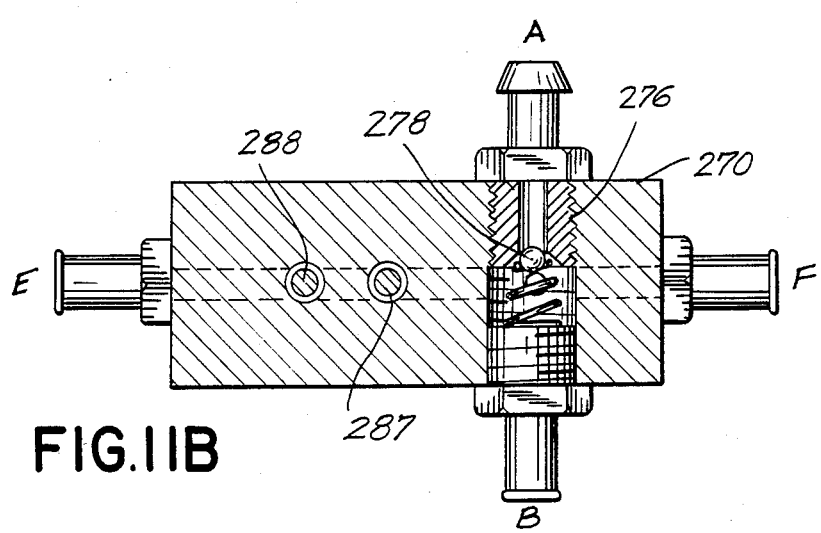
FIG.11B

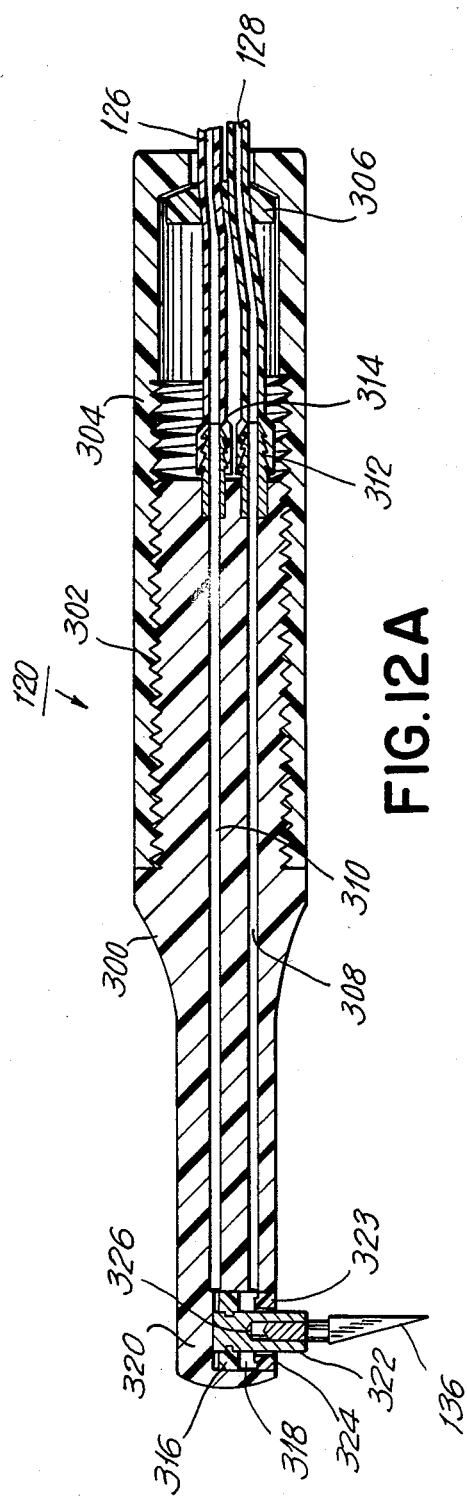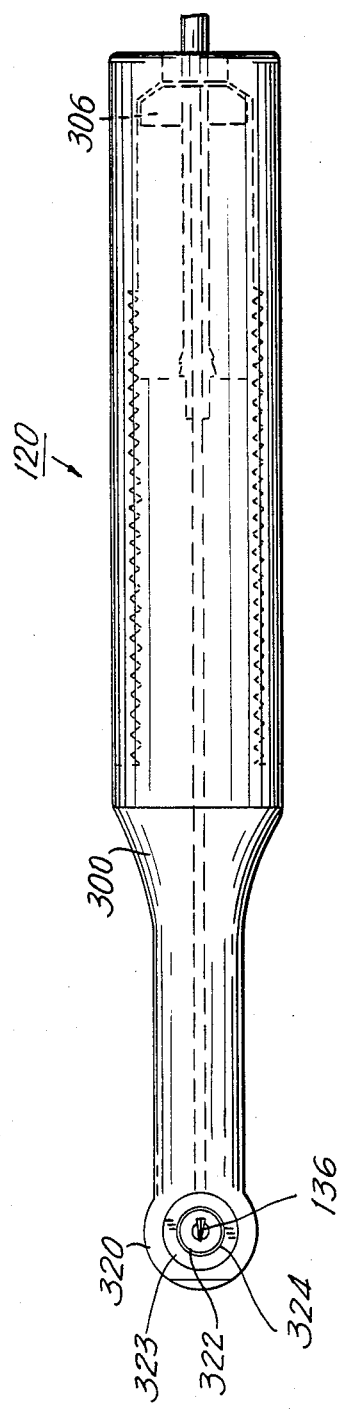
FIG.12A
FIG.12B

ORAL HYGIENE APPARATUS

BACKGROUND OF THE INVENTION

This invention relates to dental oral hygiene, and more particularly to a dental apparatus which can clean teeth and gums using a combination of a mechanical and a fluid cleaning action.

In order to treat and prevent dental disease, as well as avoiding root, surface, and interproximal cavities, it is necessary to have a regular program of dental oral hygiene. Numerous apparatus have been promoted to serve as prophylactic devices for preventing dental problems. Brushing and flossing of the teeth are well known prophylactic techniques, but are insufficient to thoroughly clean and protect the teeth. Irrigation apparatus are also available which serve to wash away the toxins produced by dental plaque. However, they do not remove the dental plaque itself. Even utilizing a pulsating action with the irrigation apparatus, still is insufficient to remove the dental plaque and provide adequate dental prophylactic.

Many types of chemical agents have been tried for removal of bacterial accumulations from the teeth. Most of these, however, also produce unwanted side effects. Even when these chemical agents are used in a milder form. They are still not effective for plaque removal. They are, however, effective for retarding the regrowth of bacterial plaque after it has been removed from the tooth surface.

More professional equipment is available for use by the dentist for interconnection to various dental apparatus. For example, U.S. Pat. No. 3,552,022 describes an apparatus which is connected to the dental drill having a tool which reciprocates and carries out mechanical cleaning of the teeth by mechanical or frictional engagement in order to remove the dental plaque. Such instrument is, however, complex, must be utilized under dental specialist conditions, and does not provide for irrigation of the tooth.

Accordingly, in providing suitable dental care, there is needed a device which can be readily utilized by consumers in caring for their own dentition, and which provides adequate cleaning of dentition by removing dental plaque while also cleaning and irrigating the surfaces and spaces between the teeth and can apply suitable chemical agents to retard the regrowth of dental plaque.

SUMMARY OF THE INVENTION

Accordingly, it is an object of the present invention to provide an apparatus for oral hygiene which avoids the aforementioned problems of prior art devices.

Another object of the present invention is to provide an apparatus for home use in the treatment and prevention of dental disease, by providing adequate cleansing action to dental surfaces.

A further object of the present invention is to provide an apparatus for oral hygiene which cleans gums and teeth by incorporating both mechanical and fluid methods of dental care.

Yet another object of the present invention is to provide an apparatus for oral hygiene which incorporates mechanical and fluid dental care while utilizing the same fluid for both the cleansing of the dental surface as well as the driving of the mechanical cleaner.

A further object of the present invention is to provide an apparatus for oral hygiene having a dental tip which reciprocates to impart mechanical or frictional cleaning of dental plaque from dental surfaces, while discharging a fluid which serves to remove the toxins and food particles as well as irrigate the dental surfaces for additional cleansing action.

Briefly, in accordance with the present invention, there is provided an apparatus for oral hygiene comprising a dental handpiece with a dental bit supported from the handpiece. The dental bit is available for imparting a mechanical cleaning action through contact with the dental surface. Associated with the dental bit there are provided fluid outlet ports. A fluid operated driving mechanism is provided in the handpiece for reciprocatingly operating the dental bit. The fluid is provided under pressure to the interior of the handpiece to actuate the driving mechanism. At the same time, a portion of the fluid is coupled for discharge through the fluid outlet ports to thereby simultaneously impart a fluid cleaning action to the dental surface in addition to the mechanical cleaning action.

The aforementioned objects, features and advantages of the invention will, in part, be pointed out with particularity and will, in part, become obvious from the following more detailed description of the invention, taken in conjunction with the accompanying drawings, which form an integral part thereof.

BRIEF DESCRIPTION OF THE DRAWINGS

In the drawings:

FIG. 6 is a schematic view of the dental apparatus of the present invention in accordance with another embodiment thereof;

FIG. 7 is a schematic detailed explanation of the operation of the dental apparatus in accordance with the embodiment shown in FIG. 6;

FIGS. 10A and 10B respectively show a side view and an end view of the pump cam shaft for use in the diaphragm pump shown in FIGS. 9A and 9B;

FIGS. 11A and 11B respectively show a cross sectional plan view and a cross sectional elevational view taken through the cross over check block for use in the embodiment shown in FIG. 6, and FIGS. 12A and 12B respectively show an elevational sectional view and a bottom view taken through the handpiece for use in conjunction with the embodiment shown in FIG. 6.

DESCRIPTION OF THE PREFERRED EMBODIMENT

Figure 1:
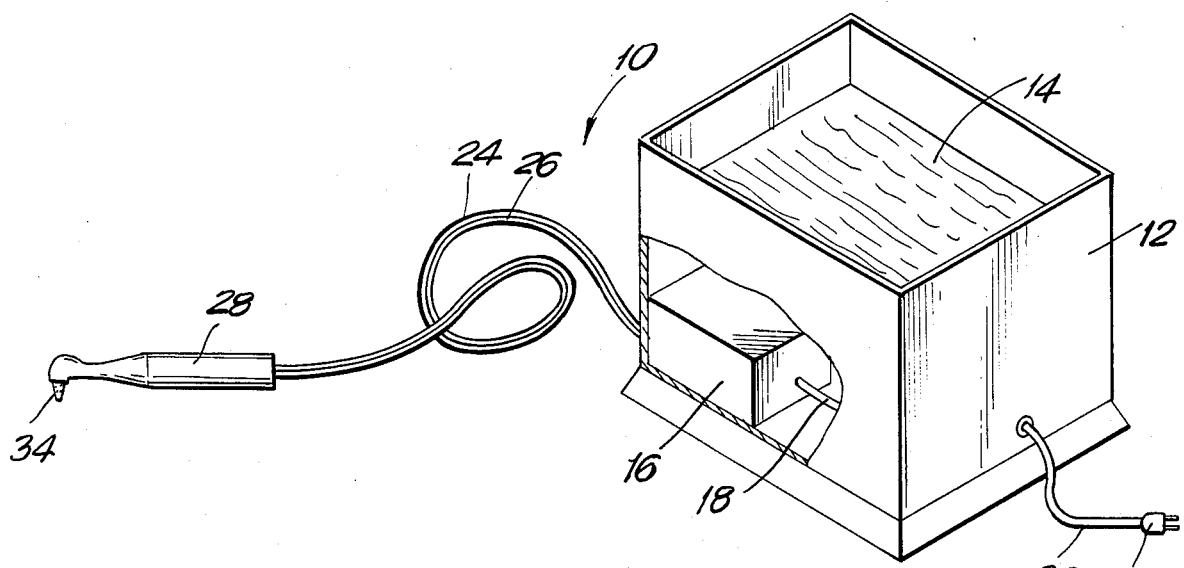
FIG. 1 is a perspective view of the dental apparatus of the present invention as intended for home use.

Referring now to FIG. 1, there is shown generally the dental apparatus 10 of the present invention including a tank 12 serving as the retainer for a fluid 14. Associated with the tank 12 is a pump 16 connected by wires 18 to outlet cord 20 terminating in plug 22 which can be inserted into a source of energy for operating the pump. A pair of adjacently coupled tubings 24, 26 respectively serve as the supply and return lines for the fluid. The supply line 24 provides the pressurized fluid to a handpiece 28, and the return line 26 provides a return of the fluid back to the tank 12. The handpiece 28 is one that can be easily manipulated by a user and supports a replaceable dental tip 34 which is utilized for the cleansing action.

Figure 2:
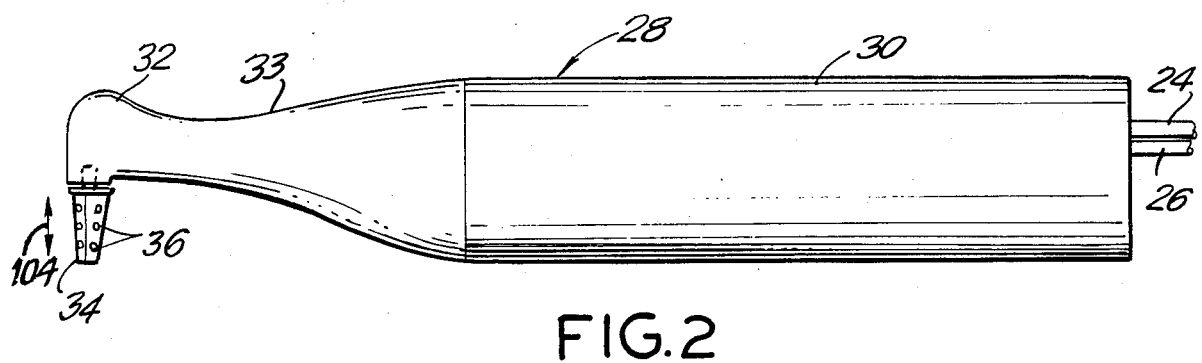
FIG. 2 is a view of the dental handpiece supporting a dental bit.

As shown in FIG. 2, the dental handpiece 28 includes a substantially elongated barrel portion 30 in which is supported the operating mechanism. A head portion 32 projects from a neck portion 33 and houses the reciprocating mechanism for manipulating the tip 34 as shown by the arrow 104. The tip 34 can be made of plastic and includes a plurality of outlet ports 36 through which fluid can be discharged. The fluid is provided through the supply line 24 and excess fluid is returned through the return line 26 both lines extending from the rear of the handpiece 28. The handpiece itself can be made of molded plastic in order to reduce its cost and make it lightweight.

Figure 3:
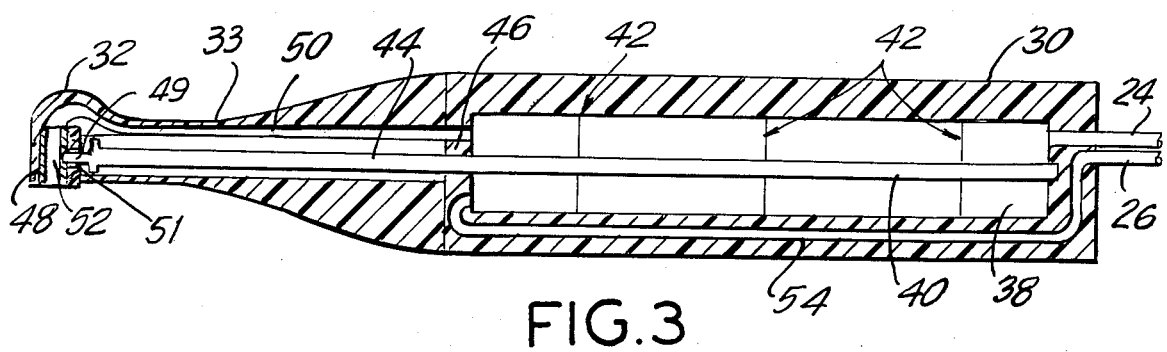
FIG. 3 is a cross sectional view taken through a dental handpiece and showing use of a fluid operated turbine providing the reciprocating action to the dental bit.

Referring now to FIG. 3, there is shown the internal operation of the apparatus in accordance with one embodiment. The handpiece barrel 30 contains a internal cavity 38 in which is provided a central shaft 40 supporting a plurality of turbine blades 42. The supply line 24 permits passage of the pressurized fluid into the chamber 38 so as to drive the turbine thereby rotating the shaft 40. The forward end of the shaft 40 continues on to rod 44 which passes through a bearing 46 and extends through neck 33 until the head portion 32 where it serves to reciprocatingly operate a support sleeve 48 in which can be inserted a dental tip of the type shown in FIG. 2. A fluid hose 50 is connected to the chamber 38 to extract a portion of the fluid, passing the extracted fluid into the aperture 52 in which the dental tip 34 is received, the fluid will be discharged through the outlet ports provided in the dental tip. A portion of the fluid from chamber 38 passes through the overflow line 54 for return through the return line 26 back to the supply tank. It will be noted that at the end of rod 44 is a finger 49 which is received in aperture 51. Finger 49 being offset with respect to the longitudinal axis of rod 44 causes the support sleeve 48 to reciprocate.

Figure 4:
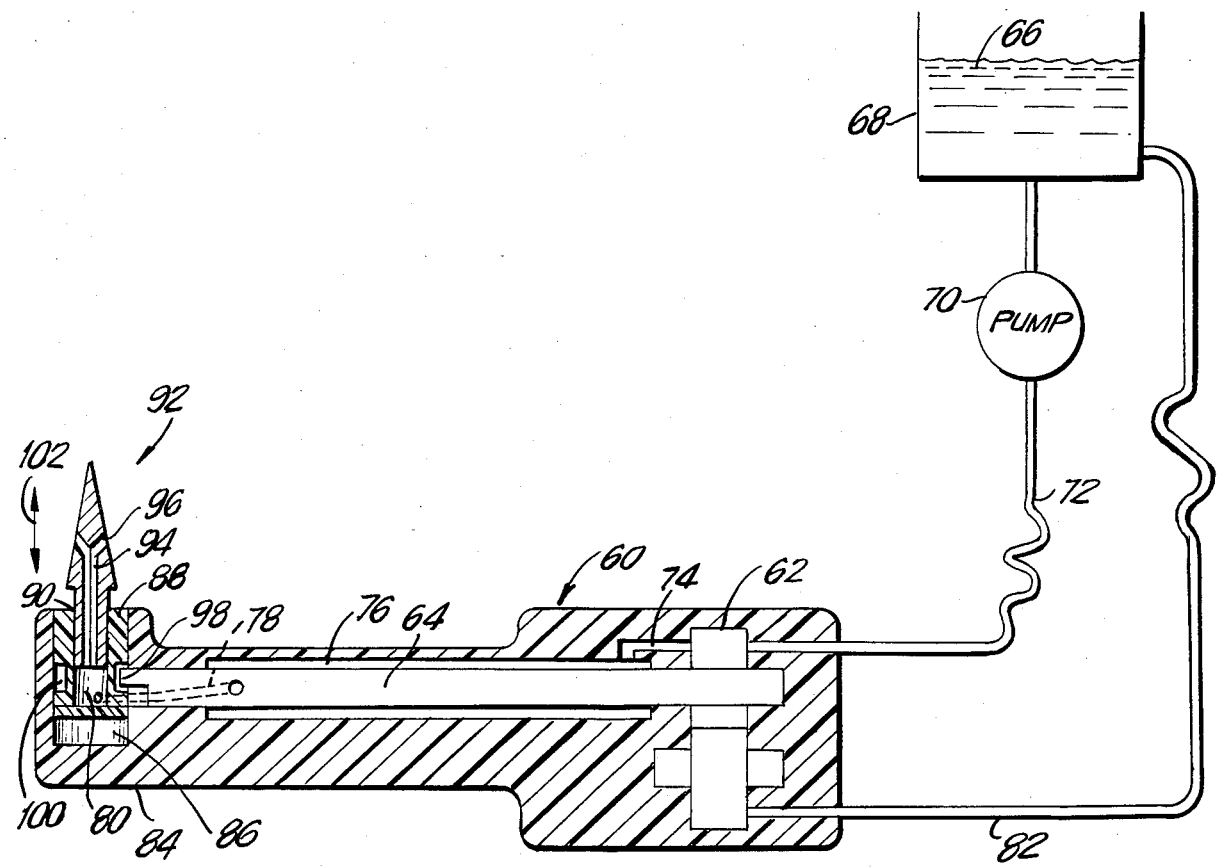
FIG. 4 is a cross sectional view through another embodiment of a dental handpiece, showing the use of a fluid operated motor for driving the dental bit and showing the passage of the fluid through the dental bit as well as connection of the fluid from the source of pressurized fluid.

FIG. 4 shows an alternate method of controlling the reciprocating action. In the dental handpiece unit 60 there is provided a fluid driven motor 62 which serves to rotate a central shaft 64. Fluid 66 is provided from the tank 68 in a pressurized condition by passing it through the pump 70 and through the supply line 72 to drive the motor 62. A portion of the fluid continues into the water hose 74 which passes around the shaft 64 in the sleeve 76 and then continues into the tube 78 for passage into the aperture space 80 provided in the tool head. The overflow portion of the fluid which is not utilized for passage in the hose 74 is permitted to overflow and pass through the return line 82.

In the head portion 84 of the dental piece 60 there is provided a cavity 86 in which is inserted a sleeve 88. The sleeve has a central aperture 80 which is typically tapered and which receives the shank portion 90 of the dental tip 92. The dental tip 92 includes a plurality of passageways 94 terminating in outlet ports 96. The fluid passing through the tube 78 and into the opening 80 is under pressure and can thereby pass through the passageways 94 and be discharged through the outlet ports 96 of the dental tip 92.

At the forward end of the shaft 64, there is provided an offset finger 98 which is received within a peripheral channel 100 provided about the sleeve 88. Rotation of the shaft 64 by means of the fluid operated motor 62 causes the finger 98 to reciprocate the sleeve 88 thereby reciprocating the dental tip 92 in a direction coaxial with its center axis, as shown by the arrows 102.

Figure 5:
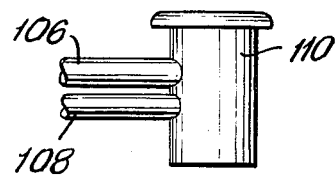
FIG. 5 is a partial view showing the interconnection of the inlet and outlet fluid lines with a connector.

As shown in FIG. 5, the supply line 106 and the return line 108 can both be connected to a common water connector 110 of a type similar to that utilized in dishwashers and other water flow mechanism. Such connector 110 would be coupled either to the pump or directly to the tank unit supplying the fluid.

In operation, the pump is turned on and the fluid under pressure is sent to the dental handpiece. The fluid serves to operate the motor, turbine, or other driving mechanism. This causes a reciprocating action on the replaceable dental tip which causes a mechanical or frictional engagement with the dental surface, thereby removing dental plaque from the dentition. At the same time, a portion of the fluid under pressure is sent to passageways provided in the dental tip and discharged through its outlet ports to simultaneously provide a fluid cleaning action on the dental surfaces. This can remove the bacteria which causes dental diseases, as well as food particles, and provides irrigation of the teeth and gum areas.

Particular fluid that can be utilized can be any of various fluid agents known to prevent dental disease and promote healing while simultaneously cleansing the teeth surface. For example, salt water, peroxide, sodium carbonate, and other similar chemical and medicinal fluid agents could be utilized.

The flow of fluid can be either continuous or intermittent. Such control can be by means of the pump which can operate in a continuous or intermittent manner, or can be controlled internally of the dental handpiece by means of a valve or other intermittent control device. Such valve or intermittent control can be connected directly to the shaft which can then open or close the flow of the fluid to the dental tip.

The tip itself can be either a rigid tip or a brush type tip. It can be either smooth or can include abrasive surfaces. Due to the design of the handpiece, the device is easy to utilize and does not require refined dexterity of the hand to carry out cleaning of the dental surface. The tips can be easily replaced without the need of a service man by simply extracting it from the retaining sleeve and inserting a replacement. Additionally, different shapes can be provided to permit its utilization on various surfaces of the teeth as well as interproximal surfaces.

Referring now to FIG. 6 there is shown a block diagram of another embodiment of the present invention wherein there is again provided a handpiece 120 which extends by means of flow tubing 122 to a central unit 124 containing a reservoir of fluid as well as necessary pumps and motors. Power to the central unit 124 comes from a pair of 12 volt DC lines 126, 128 extending from the power supplies 130, 132 which reduce the voltage from a source connected by means of a plug 134. The plug 134 can be inserted into the standard house lines and, by means of the power supply 130, 132, appropriate voltage is sent to control the present device. Dials 131, 133 can be used to control the speed of operations. A suitable dental bit 136 extends from the handpiece 120 for mechanical reciprocation against the teeth to remove dental plaque and simultaneous flow of fluid into the teeth for suitable irrigation and cleansing of the teeth.

The internal contents of the unit 124 can best be seen in FIG. 7. Within the main unit 124, there is provided a reservoir 138 containing the cleaning solution 140 of any type of chemical agent, including the types previously mentioned. Three pumps are provided. The first two pumps, 142, 144 are connected on a common shaft and timed to operate in opposition to each other by means of a single motor 146. The operation can be such that they are controlled to be timed at an operation of 180 degrees apart. The third pump 148 operates by means of a single motor 150.

A cross over relief block unit 152 is provided to control the direction of flow from the cleaning solution to the various pump and from the pumps to the handpiece through the flow lines 122. Specifically, the cleaning solution can pass along line 154 into the pump 148. All return flow back to the reservoir 138 is prevented by means of the check valve 156. The flow from the reservoir 138, as well as from the pump 148, can be directed past the valve 158 and then can flow either through valve 160 or 162. Through valve 160, the flow can either go into the pump 142 or through line 164 to the handpiece 120. Through valve 162, the flow can go to either pump 144 or through line 166 to handpiece 120.

Flow from pump 142 can only go into line 164. Likewise, flow from the pump 144 can only go into line 166. Crossover relief lines are provided between the two pumps. Specifically, line 168 is provided from pump 142 to 144, and flow relief line 170 is provided from pump 144 back to 142. The amount of pressure required on these relief valves can be suitably controlled, as will hereinafter be explained.

The power supply 30 includes a suitable speed control unit such as an SCR unit 172 and controls the speed of the motor 150. As will hereinafter be explained, the pump 148 provides the irrigation flush of the solution and accordingly, the control 172 controls the speed of the flush. In power supply 132 there is provided another speed control unit 174. Since the pumps 142 and 144 are used to operate the speed of reciprocation of the dental bit 136, the control 174 will control the speed of operation of the handpiece. Appropriate dials and dial setting can be provided on these units.

The principal of operation of the unit is as follows: The fluid 140 from the reservoir 138 initially feeds the pump 148 which operates to supply a flow to charge both the pumps 142 and 144 as well as all of the lines including lines 164, and 166 feeding the handpiece 120. All of the flow from pump 148 is utilized to flush out of the handpiece after the system is charged, and this is the flow that is utilized to provide the irrigation of the teeth during operation. Pumps 142 and 144 are timed to operate in opposition to each other and are utilized to impart a reciprocating flow on top of the steady flow coming from pump 148. The reciprocating flow alternates between the lines 164 and 166 and are fed to the handpiece to cause the dental bit 136 to reciprocate in response to this alternating flow.

Figure 8A:
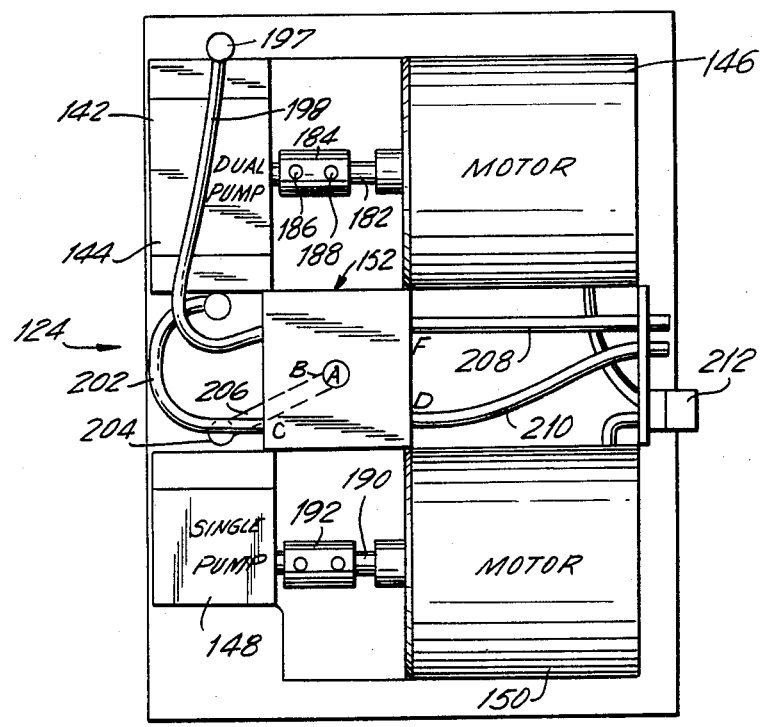
FIGS. 8A and 8B respectively show a plan view and a side view of the assembly of the unit shown in FIG. 6.
Figure 8B:
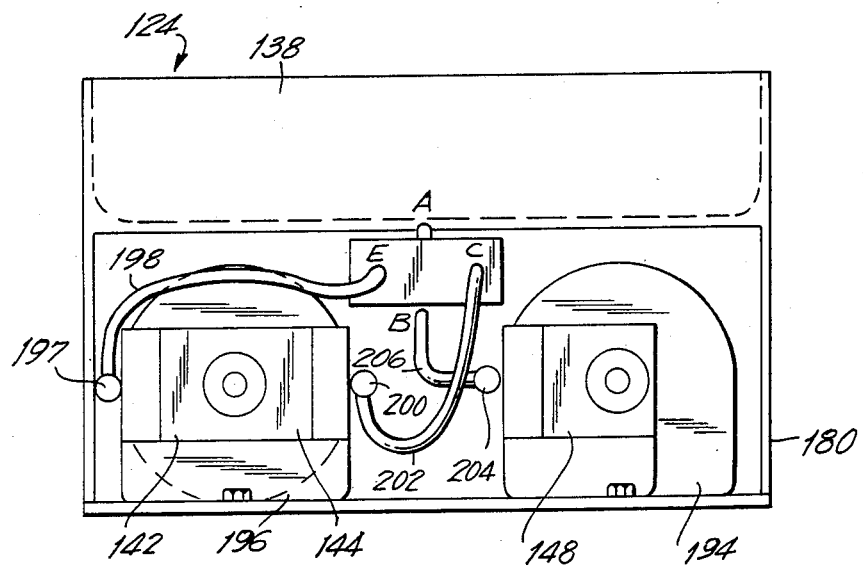

Referring now to FIGS. 8A and 8B, there is provided a structural layout and flow arrangement for the reservoir and pump unit 124 with the reservoir 138 being provided in an upper compartment and in a lower compartment 180 there is provided the motors, pumps and various flow tubes. Motor 146 is shown connected to the dual pumps 142, 144 by means of a single shaft 182 connected by means of a coupler unit 184. The coupler can include a plurality of set screws 186, 188 to clamp onto the shaft 182 and connect the dual pumps to the shaft. Motor 150 serves to operate the single pump 148 by means of another similar coupler unit 192. Suitable retaining frames 194, 196 are provided to hold the pumps in place.

The crossover check block 152 arranges the flow between the various pumps and the reservoir, and provides the flow to the handpiece. The flow from the reservoir 138 enters at the port A and can feed the pump 142 at its inlet 197 from the port E, via the tube 198. It fills the pump 144 at its inlet 200 from the port C via the tube 202. It fills the pump 148 at its inlet 204 from the port C via the tube 206. The fluid output exits from the port F through tube 208 and from port D through tube 210. The lines 208 and 210 would interconnect to the handpiece and provide the two input lines feeding the handpiece. Energization of the motors is via the electrical plug connection 212 which energizes the motors 146 and 150.

Figure 9B:
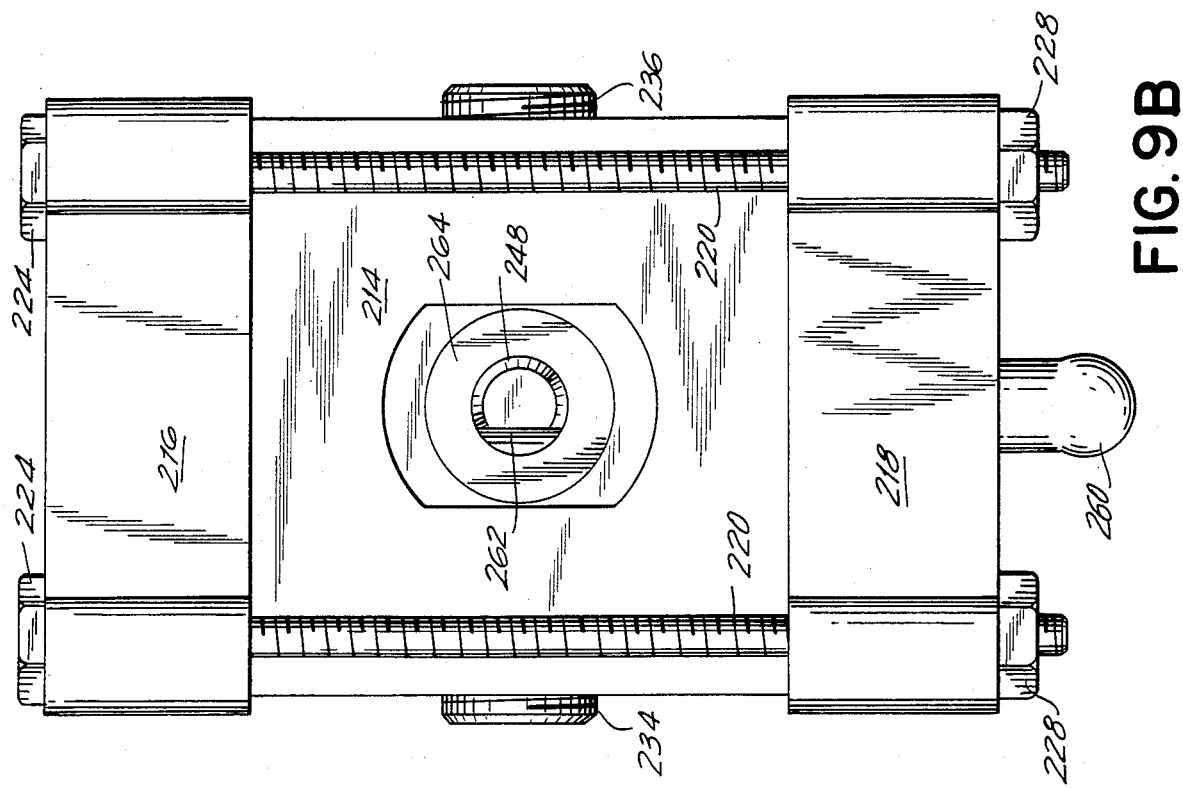
FIGS. 9A and 9B respectively show a plan view, partially broken away, and a side view of the two chamber diaphragm pump for use in the embodiment shown in FIG. 6.
Figure 9A:
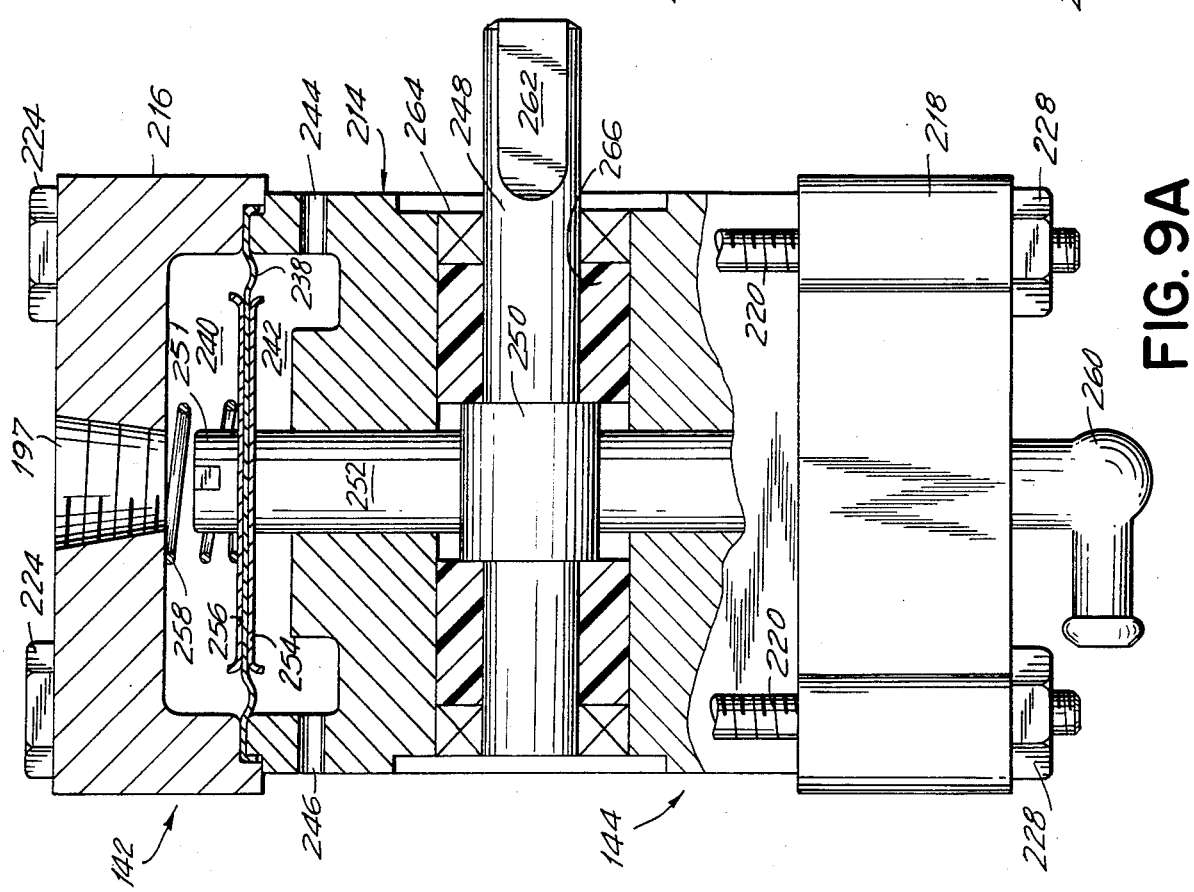

Referring now to FIGS. 9A and 9B, there is shown the dual pump unit including the pump 142 and the pump 144. The pumps include a center case 214 with opposing heads 216, 218 at either end. The unit is held together by means of four of the bolts 220, which are threaded through the heads and are retained by means of the bolt heads 224 at one end of the pump and the nuts 228 at the opposing end. Opposing pipe plugs 234, 236 are provided for mounting the pump in a support frame.

As shown with regard to the pump section 142, a cavity is defined between the head 216 and the center case 214. A flexible diaphgram 238 spans across the cavity and is clamped in place between the head and the center case so as to separate the cavity into a fluid chamber 240 and vent chamber 242. A pair of opposing vent holes 244, 246 extend through the body 214 to permit venting of the air during operation of the pump.

A single shaft 248 operates both of the pumps 142, 144 with an offset cam shaft arrangement 250 to permit operation of the pumps in opposition, as will hereinafter be explained. The cam shaft operates a piston rod 252 which extends through the case 214 and retains a pair of opposing piston plates 254, 256 by means of the screw 257, which sandwich the diaphragm 238 therebetween. A spring 258 positioned in the fluid chamber 240 acts in opposition to the piston rod 252. The port 197 is provided in which a right angle push on inlet and outlet plug 260 can be inserted, as shown at the bottom of FIG. 9A. The shaft 248 includes a flat portion 262 which enters into the coupler 184 shown in FIG. 8A, in order to drive the pump shaft by means of the motor. An oil seal 264 is provided around the sintered bronzed bushing or Teflon carbon bushing 266 which accommodates the rotating shaft 248.

In operation, the cam shaft serves to push the piston rod upwardly during a power stroke, at which time any fluid contained with the fluid chamber 240 would be exhausted through the port 197. After completion of the power stroke, the spring 258 acts downwardly against the piston rod to push the piston rod back into place thereby sucking in fluid into the port 197 to fill the fluid chamber 240. During the operation of the power and return stroke, air contained in the vent chamber 242 would be exhausted through the vents 244, 246.

As shown in FIGS. 10A and 10B, the shaft 248 includes the offset cam shaft arrangement 250 which has a larger diameter than the shaft 248. In this manner, each of the piston rods will operate in opposition so that when one piston rod has a power stroke, the other piston rod is permitted to have a return stroke under operation of its spring. This permits one of the pumps 142 to operate while the other pump 144 fills up with fluid.

Although the two chamber pumps have been described, it should be appreciated that the same type of pump and shaft arrangement can be used for the single pump 148 with only ½ of that pump being utilized or only ½ of that pump being constructed.

The crossover and check block 152 is shown in more detail in FIGS. 11A and 11B. A single housing 270 is provided having a pair of opposing flow through channels 272, 274. Flow channel 272 terminates at one end in port E which feeds pump 142 and at the other end at port F which flow out to the handpiece. Channel 274 terminates at one end in port C which feeds pump 144 and at the end in port D which feeds the handpiece. Port A connects to a vertical channel 276 which can flow downwardly into port B. The input from A is from the reservoir and port B feeds the pump 148.

A one way check valve 278 is provided along channel 276 to permit the flow from port A into the channel 276 but preventing a return flow back to the reservoir. One way check valve 280 prevents a flow from the channel 274 back into the vertical channel 276. Likewise, one way check valve 282 permits a flow into the channel 272 but prevents flow from the channel 272 to the vertical channel 276.

In this manner, the flow from the reservoir can flow down from port A and enter any of the three channels 272, 274 and 276. This permits the flow from the reservoir into all three pumps. However, the output from the two oppositely driven pumps 142, 144 from ports C and E is only permitted to flow out through the ports D and F to feed the handpiece. The output from the flush control pump 148 at port B, however, can flow to either of the other two pumps or to the handpiece, and is only prevented from flowing back to the reservoir. Pressure relief valves 284 permit flow from the channel 274 to the channel 272. Likewise, the pressure relief valve 286 permits relief flow from channel 272 into 274. By means of the projecting screws 287, 288 at the end of the relief valves, the proper pressure for such relief flow can be provided.

Each of the valves include appropriate fittings 290 at their inputs to securely hold the ports in place, as is well known in the art. The nuts 22 externally lock the tubings to the housing 270.

The handpiece unit is shown in FIGS. 12A and 12B and includes a main body portion 300 having an exterior threaded stem 302 to which is threaded a sleeve 304. The inlet tubes 126, 128 feed through a hose support plug 306 and couple onto the internally drilled holes 308, 130 by means of coupling plugs 312, 314. The holes 308, 310 respectively feed alternating flow on either side of the piston 316 provided in the chamber 318 in the head 320 of the handpiece 120. A chuck 322 is supported by the piston 316 and reciprocates as the piston 316 shuttles up and down within the cylinder 318. A seal 323 is provided at the forward end of the cylinder chamber 318. A slight space 324 is provided as a clearance space between the chuck 322 and the seal 323 to permit the flush of the fluid out of the unit and onto the dentition. A replaceable bit 136 is retained by the chuck 322 by means of a bore 326 formed in the chuck.

The fluid from the pump unit 148 serving as the flush pump provides a continuous flow of the fluid to irrigate the teeth. The pumps 142 and 144 which operate in opposition provide the fluid flow on either side of the piston 136 to reciprocate the bit 136 thereby scraping the plaque off the teeth.

It should be appreciated that instead of a flush formed in the space between the chuck and the seal, appropriate passageways could be provided directly through the chuck into the bit so that the irrigation occurs directly through the bit, as was described in connection with FIG. 2.

There has been described heretofore the best embodiment of the invention present contemplated. However, it is to be understood that various changes and modifications may be made thereto without departing from the spirit of the invention.

What is claimed:

1. An apparatus for oral hygiene comprising a dental handpiece, an axial dental bit axially supported substantially perpendicular from said handpiece imparting a mechanical cleaning action through contact with dental surfaces, fluid outlet ports associated with said dental bit, fluid operating driving means in said handpiece for mechanically operating the dental bit reciprocatingly in a direction up and down along its axis, a source of pressurized fluid for supplying actuating fluid to the interior of the handpiece to actuate the driving means, and coupling means in said handpiece for feeding at least a portion of the actuating fluid to the dental bit for pumped discharge through the outlet ports to thereby simultaneously impart a pressurized fluid cleaning action to the dental surfaces along with the mechanical cleaning action.

2. An apparatus for oral hygiene as in claim 1, wherein said dental bit comprises a replaceable dental bit.

3. An apparatus for oral hygiene as in claim 1, and comprising fluid passageways interiorly of said dental bit terminating in said outlet ports and in fluid flow communication with said coupling means.

4. An apparatus for oral hygiene as in claim 1, wherein said driving means comprises a turbine.

5. An apparatus for oral hygiene as in claim 1, wherein said driving means comprises a motor.

6. An apparatus for oral hygiene as in claim 1, and comprising a supply line from said source of pressurized fluid to said handpiece, and a return line receiving overflow fluid from the interior of the handpiece and returning it to said source of pressurized fluid.

7. An apparatus for oral hygiene as in claim 1, wherein said source of pressurized fluid comprises supply means, and pump means for pumping the fluid from said supply means.

8. An apparatus for oral hygiene as in claim 7, wherein said pump means provides a continuous flow of fluid.

9. An apparatus for oral hygiene as in claim 7, wherein said pump means provides an intermittent flow of fluid.

10. An apparatus for oral hygiene as in claim 7, wherein said supply means and said pump means form an integral unit.

11. An apparatus for oral hygiene as in claim 1, wherein said dental bit is of plastic construction.

12. An apparatus for oral hygiene as in claim 1, wherein said apparatus is a portable unit.

13. An apparatus for oral hygiene as in claim 1, wherein said fluid is saltwater.

14. An apparatus for oral hygiene as in claim 1, wherein said fluid is peroxide.

15. An apparatus for oral hygiene as in claim 1, wherein the fluid is sodium carbonate.

16. An apparatus for oral hygiene as in claim 1, wherein said driving means comprises a cylinder in said handpiece, a shuttle piston supporting the dental bit and reciprocatingly positioned in said cylinder, a pair of supply lines respectively terminating on opposing sides of said shuttle piston, and pump means for alternatingly supplying the actuating fluid to said supply lines.

17. An apparatus for oral hygiene as in claim 16, and comprising a chuck supported by said shuttle piston, said chuck interchangeably receiving a dental bit, there being a clearance fit between said chuck and said cylinder to define said outlet ports therebetween.

18. An apparatus for oral hygiene as in claim 16, wherein said pump means comprises two pumps coupled on a common shaft, and timing means on said common shaft for timing the operation of said two pumps in opposition to each other.

19. An apparatus as in claim 17, wherein said common shaft comprises an eccentric cam shaft for operating the pumps in opposition to each other.

20. An apparatus for oral hygiene as in claim 18, wherein each of said pump means comprise a pump body, a pump head secured to said body, an internal cavity defined between said pump body and head, a diaphragm stretched across said cavity and partitioning it into a fluid chamber and a vent chamber, a piston rod extending through said pump body and vent chamber and having its distal end coupled to said diaphragm, and its medial end driven by said common shaft, spring means for a return stroke of said piston after a power stroke imparted by said common shaft, port means extending through said pump head into said fluid chamber for inlet of fluid during a return stroke and discharge of the fluid during a power stroke and vent means extending through said pump body to said vent chamber.

21. An apparatus as in claim 1 wherein said fluid comprises a dental surface treating agent.

22. An apparatus as in claim 1 wherein said fluid comprises a dental surface treating agent selected from the group comprising; hydrogen peroxide, table salt, baking soda, zinc chloride, sanquinarine, chlorhexadine, epsom salts (magnesium sulfate), flourides and commercial mouth rinses, in a liquid carrier.

23. An apparatus for oral hygiene comprising a dental handpiece, an axial dental bit supported from said handpiece imparting a mechanical cleaning action through contact with dental surfaces, fluid outlet ports associated with said dental bit, fluid operating driving means in said handpiece for operating the dental bit reciprocatingly along its axis, a source of pressurized fluid for supplying actuating fluid to the interior of the handpiece to actuate the driving means, and coupling means in said handpiece for feeding at least a portion of the actuating fluid to the dental bit for pumped discharged through the outlet ports to thereby simultaneously impart a pressurized fluid cleaning action to the dental surfaces along with the mechanical cleaning action, wherein said driving means comprises a cylinder in said handpiece, a shuttle piston supporting the dental bit and reciprocatingly positioned in said cylinder, a pair of supply lines respectively terminating on opposing sides of said shuttle piston, and pump means for alternatingly supplying the actuating fluid to said supply lines, wherein said pump means comprises two pumps coupled on a common shaft, and timing means on said common shaft for timing the operation of said two pumps in opposition to each other, and further comprising a third pump continuously operating in conjunction with both said two pumps for over pressurization and providing the excess fluid needed for the fluid discharge.

24. An apparatus for oral hygiene as in claim 23, and wherein said source of fluid comprises a fluid reservoir for supplying all three pumps.

25. An apparatus for oral hygiene as in claim 24, and comprising a cross over check block including an inlet valve to permit the input of fluid from the reservoir, first and second flow channels each respectively coupling one of said two pumps to one of said two supply lines, one way flow valves for permitting the flow from said inlet valve to said first and second channels and restricting a flow in reverse, a third flow channel coupled between said third pump and said first and second channels, and a further one way valve for permitting a flow from said inlet valve to said third flow channel and restricting a flow in reverse.

26. An apparatus for oral hygiene as in claim 25, and further comprising a pair of one way relief valves for providing a relief flow path from said first channel to said second channel and from said second channel to said first channel.

27. An apparatus for oral hygiene as in claim 26, and comprising means for adjusting the relief pressure on said pair of relief valves.

* * * * *